US011705748B2

(12) United States Patent
Chan

(10) Patent No.: US 11,705,748 B2
(45) Date of Patent: Jul. 18, 2023

(54) WEARABLE GESTURE RECOGNITION DEVICE FOR MEDICAL SCREENING AND ASSOCIATED OPERATION METHOD AND SYSTEM

(71) Applicant: Russell Wade Chan, Kowloon (HK)

(72) Inventor: Russell Wade Chan, Kowloon (HK)

( * ) Notice: Subject to any disclaimer, the term of this patent is extended or adjusted under 35 U.S.C. 154(b) by 107 days.

(21) Appl. No.: 16/976,542

(22) PCT Filed: Feb. 27, 2019

(86) PCT No.: PCT/CN2019/076312
§ 371 (c)(1),
(2) Date: Aug. 28, 2020

(87) PCT Pub. No.: WO2019/165972
PCT Pub. Date: Sep. 6, 2019

(65) Prior Publication Data
US 2020/0409470 A1    Dec. 31, 2020

(30) Foreign Application Priority Data
Feb. 28, 2018    (HK) .................................. 18102884.5

(51) Int. Cl.
*G06F 3/01* (2006.01)
*H02J 7/00* (2006.01)
(Continued)

(52) U.S. Cl.
CPC ........ *H02J 7/0063* (2013.01); *A61B 5/02055* (2013.01); *A61B 5/0536* (2013.01);
(Continued)

(58) Field of Classification Search
CPC ........... A61B 2017/00207; A61B 2017/00442; A61B 5/02055; A61B 5/0536;
(Continued)

(56) References Cited

U.S. PATENT DOCUMENTS

2006/0116599 A1*   6/2006  Davis ................... A61B 5/0536
                                                          600/547
2010/0106044 A1*   4/2010  Linderman .......... A61B 5/7264
                                                          600/546
(Continued)

FOREIGN PATENT DOCUMENTS

CN          105943042        9/2016
CN          106055114        10/2016
(Continued)

OTHER PUBLICATIONS

Hong Kong Search Report.
(Continued)

*Primary Examiner* — Richard J Hong
(74) *Attorney, Agent, or Firm* — Renner Kenner Greive Bobak Taylor & Weber

(57) ABSTRACT

A wearable medical screening device using electrical impedance tomogram and associated operation method. The wearable medical screening device includes electrodes, signal generator, and signal processor. The electrodes are arranged to be arranged on a body part of a wearer. The signal generator is arranged to provide a signal to at least one of the electrodes for transmission of a respective excitation signal to the body part of the wearer. The signal processor is arranged to process respective response signal received by at least one of the remaining electrodes as a result of the respective excitation signal, for determination of an electrical impedance tomogram for real-time preliminary medical screening of a disease associated with body part on which the wearable medical screening device is worn.

22 Claims, 11 Drawing Sheets

(51) Int. Cl.
*A61B 5/0205* (2006.01)
*A61B 5/0536* (2021.01)
*A61B 5/00* (2006.01)

(52) U.S. Cl.
CPC ............ *A61B 5/681* (2013.01); *A61B 5/7267* (2013.01); *G06F 3/017* (2013.01)

(58) Field of Classification Search
CPC ..... A61B 5/4041; A61B 5/681; A61B 5/7267; A61B 5/6823; A61B 5/1101; A61B 5/7282; A61B 5/7264; A61B 5/0022; A61B 5/053; A61B 5/7203; G06F 3/014; G06F 3/017; G06F 3/015; G06F 3/011; G06N 20/00; H02J 7/0063; G16H 50/70
See application file for complete search history.

(56) References Cited

U.S. PATENT DOCUMENTS

| | | | | |
|---|---|---|---|---|
| 2012/0172682 | A1* | 7/2012 | Linderman | G06F 3/015 600/300 |
| 2013/0013331 | A1* | 1/2013 | Horseman | A61B 5/0022 705/2 |
| 2013/0102872 | A1* | 4/2013 | Park | A61B 5/0536 600/372 |
| 2013/0232095 | A1 | 9/2013 | Tan et al. | |
| 2014/0094675 | A1* | 4/2014 | Luna | A61B 5/1101 600/386 |
| 2015/0272501 | A1* | 10/2015 | Maceachern | A61B 5/6823 600/301 |
| 2016/0100791 | A1* | 4/2016 | Arad (Abboud) | A61B 5/053 600/547 |
| 2017/0156662 | A1* | 6/2017 | Goodall | A61B 5/7282 |
| 2017/0290077 | A1 | 10/2017 | Nilsson et al. | |
| 2018/0153430 | A1* | 6/2018 | Ang | A61B 5/7203 |
| 2018/0360379 | A1* | 12/2018 | Harrison | G06F 3/014 |
| 2019/0033974 | A1* | 1/2019 | Mu | G06F 3/011 |

FOREIGN PATENT DOCUMENTS

| | | |
|---|---|---|
| CN | 106249853 | 12/2016 |
| CN | 106527670 | 3/2017 |
| CN | 106570368 | 4/2017 |
| CN | 106575150 | 4/2017 |
| CN | 105608432 | 2/2019 |
| WO | 2016210441 | 12/2016 |
| WO | 2018011720 | 1/2018 |

OTHER PUBLICATIONS

European Search Report.
"Advancing Hand Gesture Recognition with High Resolution Electrical Impedance Tomography". User Interface Software and Technology. ACM. 2 Penn Plaza. Suite 701 New York NY 10121-0701 USA. Oct. 16, 2016 (Oct. 16, 2016). pp. 843-850. XP058299708. DOI: 10.1145/2984511.2984574 ISBN: 978-1-4503-4189-9.

* cited by examiner

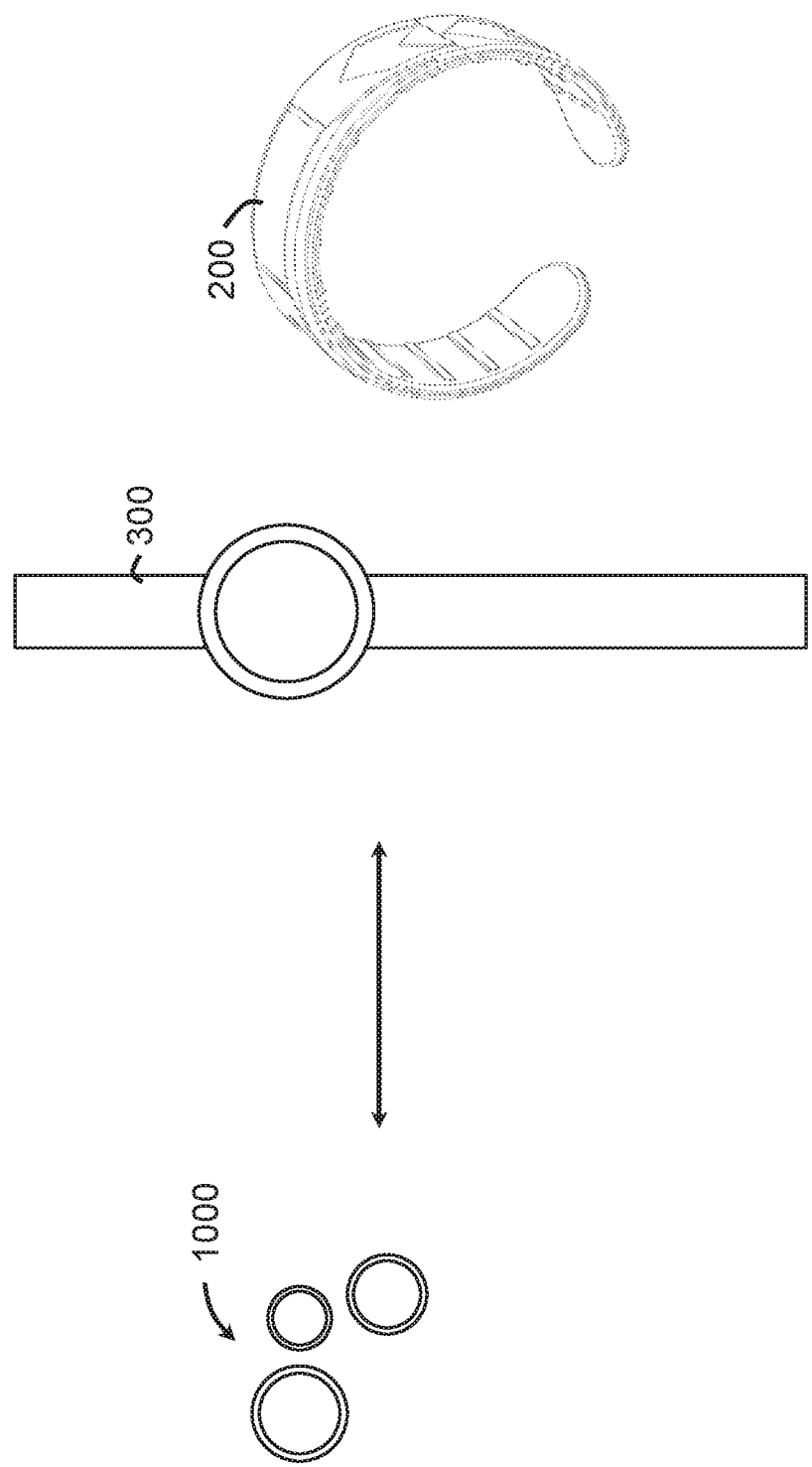

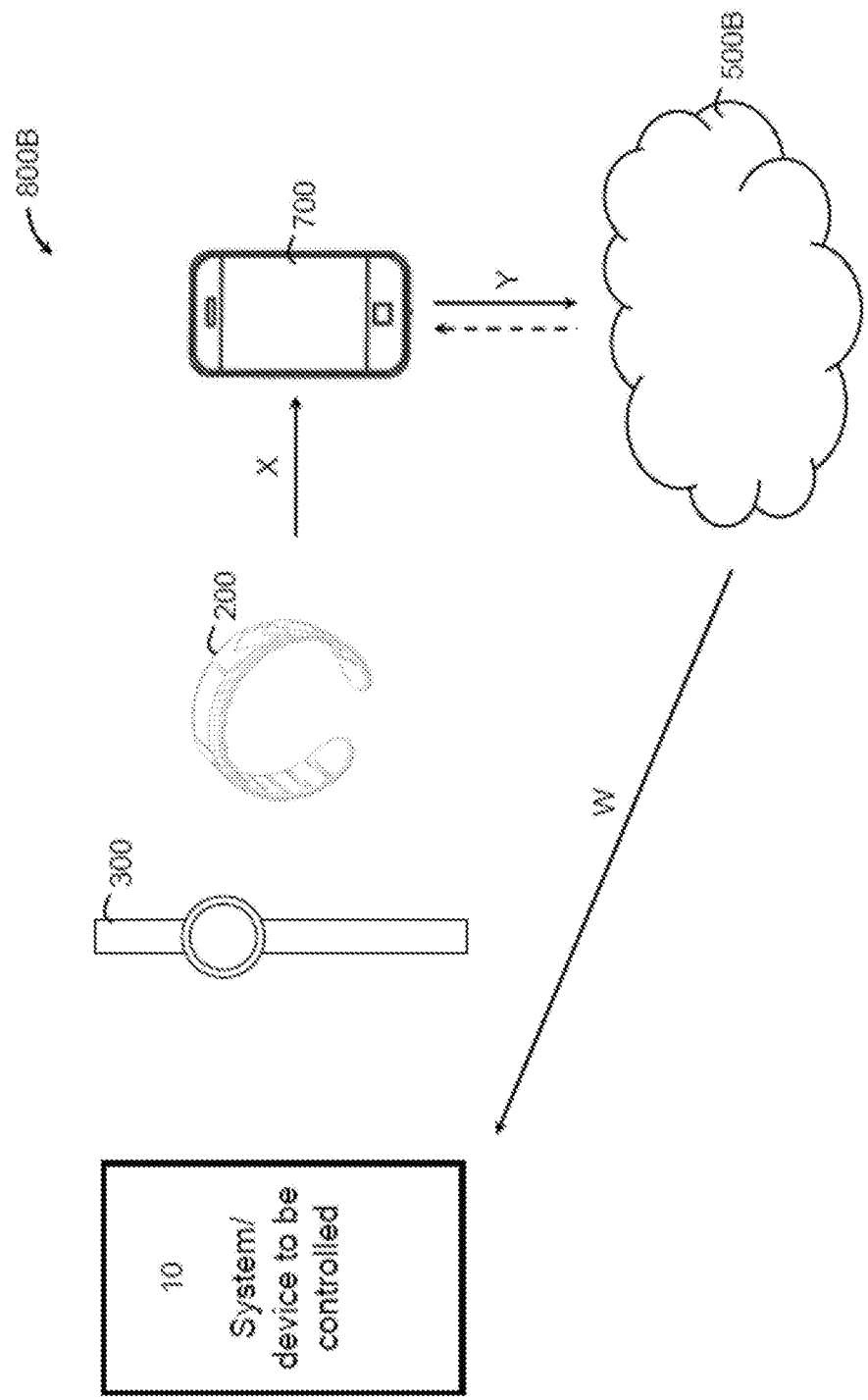

WEARABLE GESTURE RECOGNITION DEVICE FOR MEDICAL SCREENING AND ASSOCIATED OPERATION METHOD AND SYSTEM

TECHNICAL FIELD

The invention relates to a wearable gesture recognition device and its associated operation method and system.

BACKGROUND

With the rapid advancement in technologies driven by consumers' craving for increasingly portable devices with advanced functions, wearable devices have become extremely popular in the consumer market in recent years.

Generally, a wearable electronic device can be worn on any part of the body of the user while providing one or more functions. For example, a digital watch can be worn on the user's wrist to show time, a smart glass that can be worn on a user's head etc. as a portable phone and camera.

Some existing wearable electronic device can provide gesture recognition function, by virtue of an IMU of the device. By detecting movement and rotation using the IMU, movement of the wearable electronic device can be detected and used to infer movement of the user. However, gesture recognition function of this sort is often crude, prone to error, and hence unreliable.

There remains a need for wearable electronic device can provide fine gesture recognition function with a reasonable degree of accuracy for extended applications.

SUMMARY OF THE INVENTION

In accordance with a first aspect of the invention, there is provided a method of gesture recognition using a wearable gesture recognition device, comprising: arranging a plurality of electrodes to be on a body part of a wearer; providing a signal to at least one of the plurality of electrodes for transmission of a respective excitation signal to the body part of the wearer; and processing respective response signal received by at least one of the remaining electrodes as a result of the respective excitation signal, for determination of an electrical impedance tomogram for gesture recognition. The excitation signal may be attenuated by the body part.

The electrodes may be contact-type that is arranged to contact the wearer's body part when the wearable gesture recognition device is worn, or they may be non-contact type that is not arranged to contact the wearer's body part when the wearable gesture recognition device is worn.

In one embodiment of the first aspect, the method further includes communicating information and data between the wearable gesture recognition device and one or both of: an external electronic device and a server.

In one embodiment of the first aspect, the method further includes reconstructing an electrical impedance tomogram based on the signals processed by the signal processor. The reconstruction may be performed at the wearable gesture recognition device, at the external electronic device or server, or at both.

In one embodiment of the first aspect, the method further includes comparing the reconstructed electrical impedance tomogram with predetermined electrical impedance tomograms in a database to determine a matching, wherein the predetermined electrical impedance tomograms each correspond to a respective gesture; and determining, based on the determined matching, a gesture associated with the reconstructed electrical impedance tomogram. The comparison and determination may be performed at the wearable gesture recognition device, at the external electronic device or server, or at both.

In one embodiment of the first aspect, the method further includes training the database based on machine learning method using one or both of: the signals received from the communication module and reconstructed electrical impedance tomogram. The training may be performed at the wearable gesture recognition device, at the external electronic device or server, or at both.

In one embodiment of the first aspect, the method further includes determining a response based on the determined gesture. The determination may be performed at the wearable gesture recognition device, at the external electronic device or server, or at both.

In one embodiment of the first aspect, the method further includes transmitting signals indicative of the determined response to a device or system to be controlled to affect operation thereof. The transmission may be from the wearable gesture recognition device or from the external electronic device or server.

In one embodiment of the first aspect, the communication is wireless.

In one embodiment of the first aspect, the server comprises a cloud computing server, and the external electronic device comprises a mobile phone, a computer, or a tablet.

In one embodiment of the first aspect, the plurality of electrodes are arranged to operate as both transmission electrode and receiving electrode.

In one embodiment of the first aspect, the method further includes selecting at least one of the plurality of electrodes as transmission electrode and at least one of the remaining electrodes as receiving electrode. The transmission and receiving may be repeated for numerous different electrode configurations, i.e., with different electrodes being used for transmission electrode(s) and receiving electrode(s).

In one embodiment of the first aspect, the plurality of electrodes are in the form of strips that are spaced apart from each other. Alternatively, the electrodes can be in the form of points, pints, needles, etc.

In one embodiment of the first aspect, the method further includes determining movement of the wearable gesture recognition device to affect determination of the electrical impedance tomogram. For example, if it is determined that the movement of the wearable gesture recognition device is excessive or too sudden, the signals from the electrodes may be discarded.

In one embodiment of the first aspect, the method further includes detecting physiological signals of the wearer to affect determination of the electrical impedance tomogram. For example, if it is determined that the movement of the physiological signals is abnormal, the signals from the electrodes may be discarded.

In one embodiment of the first aspect, the wearable gesture recognition device is arranged to be wrist-worn for recognition of hand gesture. Hand gesture, may refer to the movement (translation, rotation, etc.) of the finger, wrist, palm, etc. The wearable gesture recognition device may be arranged to be worn on a different body part, for recognition of gesture or movement of another body part.

In accordance with a second aspect of the invention, there is provided a system of gesture recognition using a wearable gesture recognition device, comprising: a plurality of electrodes arranged to be arranged on a body part of a wearer; means for providing a signal to at least one of the plurality of electrodes for transmission of a respective excitation signal to the body part of the wearer; and means for processing respective response signal received by at least one of the remaining electrodes as a result of the respective excitation signal, for determination of an electrical impedance tomogram for gesture recognition. The excitation signal may be attenuated by the body part.

The electrodes may be contact-type that is arranged to contact the wearer's body part when the wearable gesture recognition device is worn, or they may be non-contact type that is not arranged to contact the wearer's body part when the wearable gesture recognition device is worn.

In one embodiment of the second aspect, the system further includes means for communicating information and data between the wearable gesture recognition device and one or both of: an external electronic device and a server.

In one embodiment of the second aspect, the system further includes means for reconstructing an electrical impedance tomogram based on the signals processed by the signal processor. The reconstruction may be performed at the wearable gesture recognition device, at the external electronic device or server, or at both.

In one embodiment of the second aspect, the system further includes means for comparing the reconstructed electrical impedance tomogram with predetermined electrical impedance tomograms in a database to determine a matching, wherein the predetermined electrical impedance tomograms each correspond to a respective gesture; and means for determining, based on the determined matching, a gesture associated with the reconstructed electrical impedance tomogram. The comparison and determination may be performed at the wearable gesture recognition device, at the external electronic device or server, or at both.

In one embodiment of the second aspect, the system further includes means for determining a response based on the determined gesture. The determination may be performed at the wearable gesture recognition device, at the external electronic device or server, or at both.

In one embodiment of the second aspect, the system further includes means for training the database based on machine learning method using one or both of: the signals received from the communication module and reconstructed electrical impedance tomogram. The training may be performed at the wearable gesture recognition device, at the external electronic device or server, or at both.

In one embodiment of the second aspect, the system further includes means for transmitting signals indicative of the determined response to a device or system to be controlled to affect operation thereof. The transmission may be from the wearable gesture recognition device or from the external electronic device or server.

In one embodiment of the second aspect, the communication is wireless.

In one embodiment of the second aspect, the server comprises a cloud computing server, preferably implemented by combination of software and hardware, and the external electronic device comprises a mobile phone, a computer, or a tablet.

In one embodiment of the second aspect, the plurality of electrodes are arranged to operate as both transmission electrode and receiving electrode.

In one embodiment of the second aspect, the system further includes means for selecting at least one of the plurality of electrodes as transmission electrode and at least one of the remaining electrodes as receiving electrode. The transmission and receiving may be repeated for numerous different electrode configurations, i.e., with different electrodes being used for transmission electrode(s) and receiving electrode(s).

In one embodiment of the second aspect, the plurality of electrodes are in the form of strips that are spaced apart from each other. Alternatively, the electrodes can be in the form of points, pints, needles, etc.

In one embodiment of the second aspect, the system further includes means for determining movement of the wearable gesture recognition device to affect determination of the electrical impedance tomogram. For example, if it is determined that the movement of the wearable gesture recognition device is excessive or too sudden, the signals from the electrodes may be discarded.

In one embodiment of the second aspect, the system further includes means for detecting physiological signals of the wearer to affect determination of the electrical impedance tomogram. For example, if it is determined that the movement of the physiological signals is abnormal, the signals from the electrodes may be discarded.

In one embodiment of the second aspect, the wearable gesture recognition device is arranged to be wrist-worn for recognition of hand gesture. Hand gesture, may refer to the movement (translation, rotation, etc.) of the finger, wrist, palm, etc.

In accordance with a third aspect of the invention, there is provided wearable gesture recognition device, comprising: a plurality of electrodes arranged to be arranged on a body part of a wearer; a signal generator arranged to provide a signal to at least one of the plurality of electrodes for transmission of a respective excitation signal to the body part of the wearer; and a signal processor arranged to process respective response signal received by at least one of the remaining electrodes as a result of the respective excitation signal, for determination of an electrical impedance tomogram for gesture recognition. The excitation signal may be attenuated by the body part.

The electrodes may be contact-type that is arranged to contact the wearer's body part when the wearable gesture recognition device is worn, or they may be non-contact type that is not arranged to contact the wearer's body part when the wearable gesture recognition device is worn.

In one embodiment of the third aspect, the wearable gesture recognition device further includes a communication module arranged to communicate information and data between the wearable gesture recognition device and one or both of: an external electronic device and a server.

In one embodiment of the third aspect, the communication module is arranged to transmit, to the external electronic device or the server, signals processed by the signal processor, for determination of the electrical impedance tomogram for gesture recognition.

In one embodiment of the third aspect, the external electronic device or the server is arranged to: reconstruct an electrical impedance tomogram based on signals received from the communication module.

In one embodiment of the third aspect, the external electronic device or the server is arranged to: compare the reconstructed electrical impedance tomogram with predetermined electrical impedance tomograms in a database to determine a matching, wherein the predetermined electrical impedance tomograms each correspond to a respective gesture; and determine, based on the determined matching, a gesture associated with the reconstructed electrical impedance tomogram.

In one embodiment of the third aspect, the external electronic device or the server is arranged to: determine a response based on the determined gesture.

In one embodiment of the third aspect, the external electronic device or the server is further arranged to: train the database based on machine learning method using one or both of: the signals received from the communication module and reconstructed electrical impedance tomogram.

In one embodiment of the third aspect, the external electronic device or the server is further arranged to transmit signals indicative of the determined response to a device or system to be controlled to affect operation thereof.

In one embodiment of the third aspect, the external electronic device or the server is further arranged to transmit signals indicative of the determined response to the wearable gesture recognition device.

In one embodiment of the third aspect, the communication module is arranged to receive, from the external electronic device or the server: signals indicative of a gesture determined based on the determined electrical impedance tomogram, or signals indicative of a response determined based on the determined electrical impedance tomogram.

In one embodiment of the third aspect, the communication module comprises a wireless communication module. The wireless communication module preferably includes a Bluetooth module, but it may alternatively or also include LTE, Wi-Fi, NFC, ZigBee, etc. communication modules.

In one embodiment of the third aspect, the external electronic device comprises a mobile phone, a computer, or a tablet.

In one embodiment of the third aspect, the server comprises a cloud computing server, preferably implemented by combination of software and hardware.

In one embodiment of the third aspect, the plurality of electrodes are arranged to operate as both transmission electrode and receiving electrode. For example, electrode A can operate as a transmission electrode at time t, and as a receiving electrode at time t+Δt.

In one embodiment of the third aspect, the wearable gesture recognition device further comprises a multiplexer arranged to select at least one of the plurality of electrodes as transmission electrode and to select at least one of the remaining electrodes as receiving electrode.

In one embodiment of the third aspect, the plurality of electrodes are in the form of strips that are spaced apart from each other. Alternatively, the electrodes can be in the form of points, pints, needles, etc.

In one embodiment of the third aspect, the plurality of electrodes are spaced apart substantially equally.

In one embodiment of the third aspect, the wearable gesture recognition device further comprises a flexible body arranged to be worn by the wearer and on which the plurality of electrodes are arranged. Preferably, the flexible body is arranged to be fit onto the wearer by inherent resilience.

In one embodiment of the third aspect, the wearable gesture recognition device further comprises one or more of: a display; one or more actuators or a touch-sensitive display for receiving input from the wearer; and a power source. The power source is preferably a rechargeable power source, and optionally arranged to be inductively charged.

In one embodiment of the third aspect, the wearable gesture recognition device further comprises an IMU arranged to determine movement of the wearable gesture recognition device to affect determination of the electrical impedance tomogram.

In one embodiment of the third aspect, the wearable gesture recognition device further comprises one or more biosensors arranged to detect physiological signals of the wearer to affect determination of the electrical impedance tomogram. The one or more biosensors may be any of: a blood oxygen level sensor; a pulse rate sensor; a pressure sensor; a temperature sensor; a heart rate sensor; and an EMG detector.

In one embodiment of the third aspect, the wearable gesture recognition device further comprises a GPS module arranged to determine location of the wearable gesture recognition device. The determined location may optionally be used to affect determination of the electrical impedance tomogram.

In one embodiment of the third aspect, the wearable gesture recognition device further comprises a microphone, or like speech input device, operably connected with a processor, for processing sound received. In one example, this arrangement enables the device to be voice controlled. In yet another example, this arrangement enables the speech of a user be transformed into text displayed on the display screen of the device.

In one embodiment of the third aspect, the wearable gesture recognition device further comprises a slot or dock arranged to receive a sim card, data card, etc., for extending the memory or functionality (e.g., communication and connectivity) of the device.

In one embodiment of the third aspect, the wearable gesture recognition device is arranged to be wrist-worn for recognition of hand gesture. Hand gesture, may refer to the movement (translation, rotation, etc.) of the finger, wrist, palm, etc.

In accordance with a fourth aspect of the invention there is provided a gesture recognition system, comprising: a wearable gesture recognition device of the first aspect, and one or both of an external electronic device and a server, arranged to be in data communication with the wearable gesture recognition device.

In one embodiment of the fourth aspect, the external electronic device and server are the external electronic device and server of the second aspect.

In one embodiment of the fourth aspect, the system further comprises a charger for charging the wearable gesture recognition device. The charger may be a wireless charger arranged to charge the wearable gesture recognition device wirelessly.

BRIEF DESCRIPTION OF THE DRAWINGS

Embodiments of the invention will now be described, by way of example, with reference to the accompanying drawings in which:

FIG. 7 is an illustration of a ring accessory arranged to be used with the wearable gesture recognition device of FIGS. 2 to 3B in accordance with one embodiment of the invention;

FIG. 8B is a system incorporating a wearable gesture recognition device in accordance with one embodiment of the invention;

DETAILED DESCRIPTION OF THE PREFERRED EMBODIMENT

Figure 1:
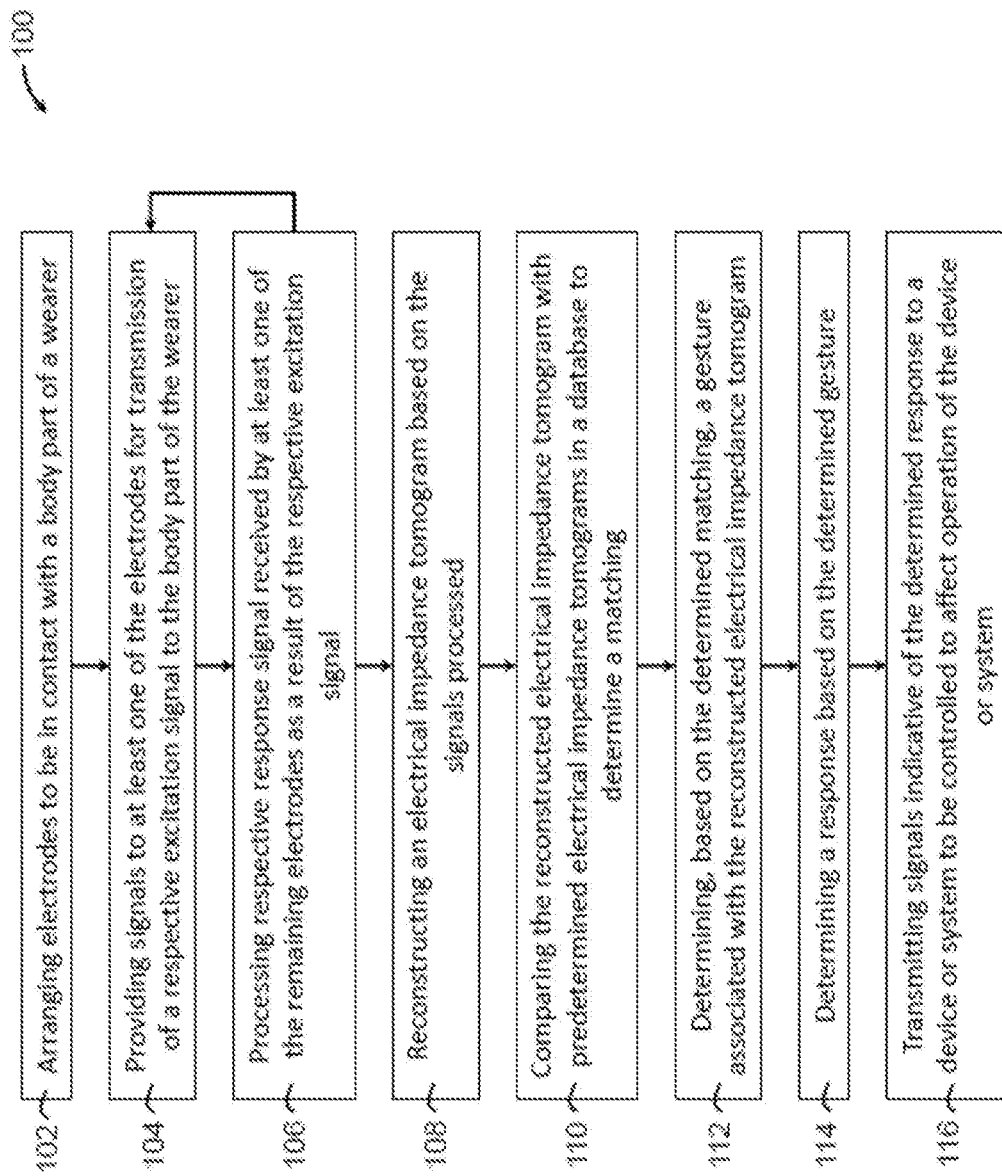
FIG. 1 is a flow diagram showing a gesture recognition method implemented using a wearable gesture recognition device in accordance with one embodiment of the invention.

FIG. 1 shows a gesture recognition method 100 implemented using a wearable gesture recognition device in accordance with one embodiment of the invention. The method begins in step 102, wherein a wearable gesture recognition device is worn by a user. The wearable gesture recognition device includes electrodes arranged to be arranged on a body part of the user. In a preferred embodiment, the body part may be a wrist. The electrodes may be contact type or non-contact type.

In step 104, signals are provided to at least one of the electrodes for transmission of a respective excitation signal to the body part of the wearer. The excitation signal may attenuate as it travels through the body part of the wearer. The signals provided may comprise 30 kHz to 50 kHz waveform. The excitation signal may have a combination of different frequency, phase, amplitude, etc. For example, the excitation signal may be formed by waveforms of (1) different shape: square wave, rectangular wave, triangular wave, comb wave, sinusoidal wave, etc.; different sweeping frequency or amplitude: chirp function, etc.; (2) different modulation: amplitude modulation or frequency modulation; or (4) any of their combination. In one example, one of the electrodes is arranged to transmit an excitation signal to the body part of the wearer. In another example, two electrodes are arranged to simultaneously transmit respective excitation signals to the body part of the wearer. The two signals may have same or different properties. The excitation signal may attenuate as it travels through the user.

In step 106, one or more of the remaining electrodes not used for transmission may receive response signal as a result of the respective excitation signal. In one example, the excitation may travel through the body part of the user and picked up by one or more of the remaining electrodes. The time that the response signal is received may be different for different electrodes.

Preferably, steps 104 and 106 are repeated with different electrodes acting as transmission electrode and receiving electrodes, to obtain more information on the response provided by the body part of the user. In one example, the transmission and receive may even be repeated for the same electrodes.

After obtaining sufficient data or information in steps 104 and 106, or after completing an excitation cycle in steps 104 and 106, the method proceeds to step 108, in which an electrical impedance tomogram is reconstructed based on the signals received and processed. The reconstruction may be performed at the wearable gesture recognition device or may be performed at a server or external electronic device operably connected with the wearable gesture recognition device.

Then, in step no, the reconstructed electrical impedance tomogram is compared with predetermined electrical impedance tomograms in a database to determine a matching. More particular, the reconstructed electrical impedance tomogram is compared with predetermined electrical impedance tomograms in a database to determine which predetermined electrical impedance tomogram is most similar to the reconstructed electrical impedance tomogram. The database may be provided the wearable gesture recognition device, or the server or external electronic device, or both. In one embodiment, the database may be trained based on machine learning method using the processed signals and the reconstructed electrical impedance tomogram. With training, the database can be trained to improve the comparison speed and accuracy.

In step 112, based on the determined matching, the gesture associated with the reconstructed electrical impedance tomogram is determined. The determination may be based on a look-up from the database or a separate database, which associates different predetermined electrical impedance tomogram with predetermined gestures.

In step 114, based on the gesture determined, a response is determined. For example, the response may be determined by looking up a database that associates different predetermined gesture with predetermined responses. The response in the present embodiment may be a control signal to affect operation of an external electronic device or system, or may be a signal to generate a result on an external electronic device or system. In step 116, signals indicative of the determined response is transmitted to a device or system to be controlled to affect operation of the device or system.

Figure 2:
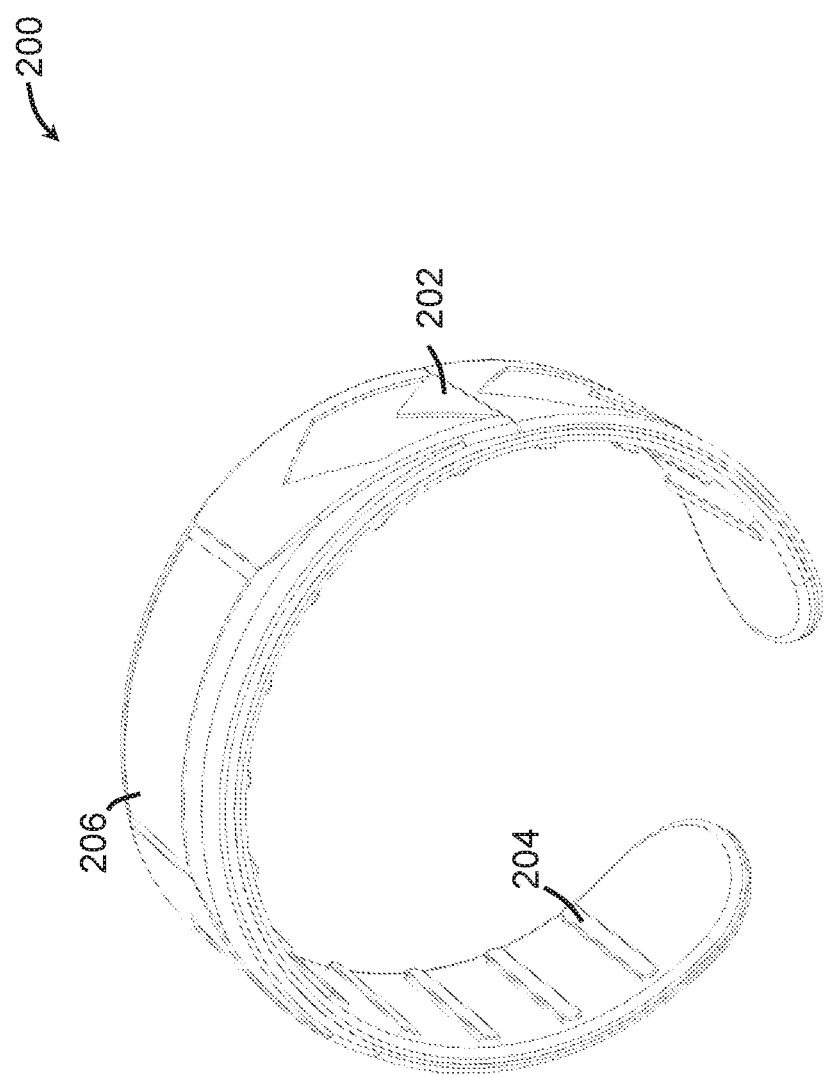
FIG. 2 is an illustration of a wearable gesture recognition device, in the form of a wristband, in accordance with one embodiment of the invention.

FIG. 2 shows a wearable gesture recognition device, in the form of a wristband 200, in accordance with one embodiment of the invention. The wristband 200 includes a flexible body 202 arranged to be worn by the wearer. Preferably, the flexible body 202 is arranged to be fit onto the wearer by inherent resilience. The flexible body 202 may thus be adapted to be worn by users with different wrist sizes.

Multiple electrodes 204, operable as both transmission and receiving electrodes, are arranged on the inner surface of the wristband 200. The electrodes 204 are in the form of strips that are spaced apart from each other. In the present embodiment, the electrodes 204 are spaced apart substantially equally. However, in some embodiments this is not necessary. The number of electrodes 204 may any number larger than 2. The electrodes 204 may be made of copper, aluminum, or metal alloy. A display 206 is arranged on the outer surface of the wristband 200. The display 206 may be touch sensitive to provide a means for the user to interact with (provide input to) the wristband 200. Various internal structure of the wristband 200 will be described in further detail below.

FIGS. 3A and 3B show a wearable gesture recognition device, in the form of a watch 300, in accordance with one embodiment of the invention. The watch 300 includes a watch face 302 providing a display. Flexible watch straps 303 are connected to the watch face. Preferably, a clasp or connector 305 is provided at the open ends of at least one of the watch strap to allow the watch to be worn. Multiple electrodes 304, operable as both transmission and receiving electrodes, are arranged on the inner surface of the watch straps 303. The watch 300 also includes an actuator 308 for receiving user input. The actuator 308 may be in the form of a dial, a button, a slider, etc. Various internal structure of the watch 300 will be described in further detail below.

Figure 3:
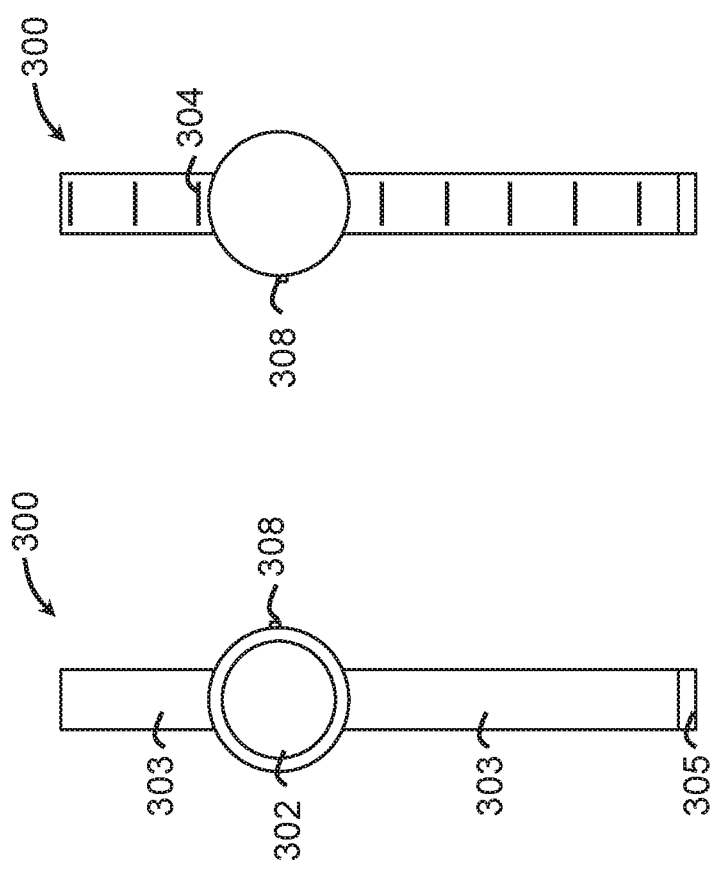
FIG. 3A is a front view of a wearable gesture recognition device, in the form of a watch, in accordance with one embodiment of the invention.
FIG. 3B is a rear view of the wearable gesture recognition device of FIG. 3A
Figure 4:
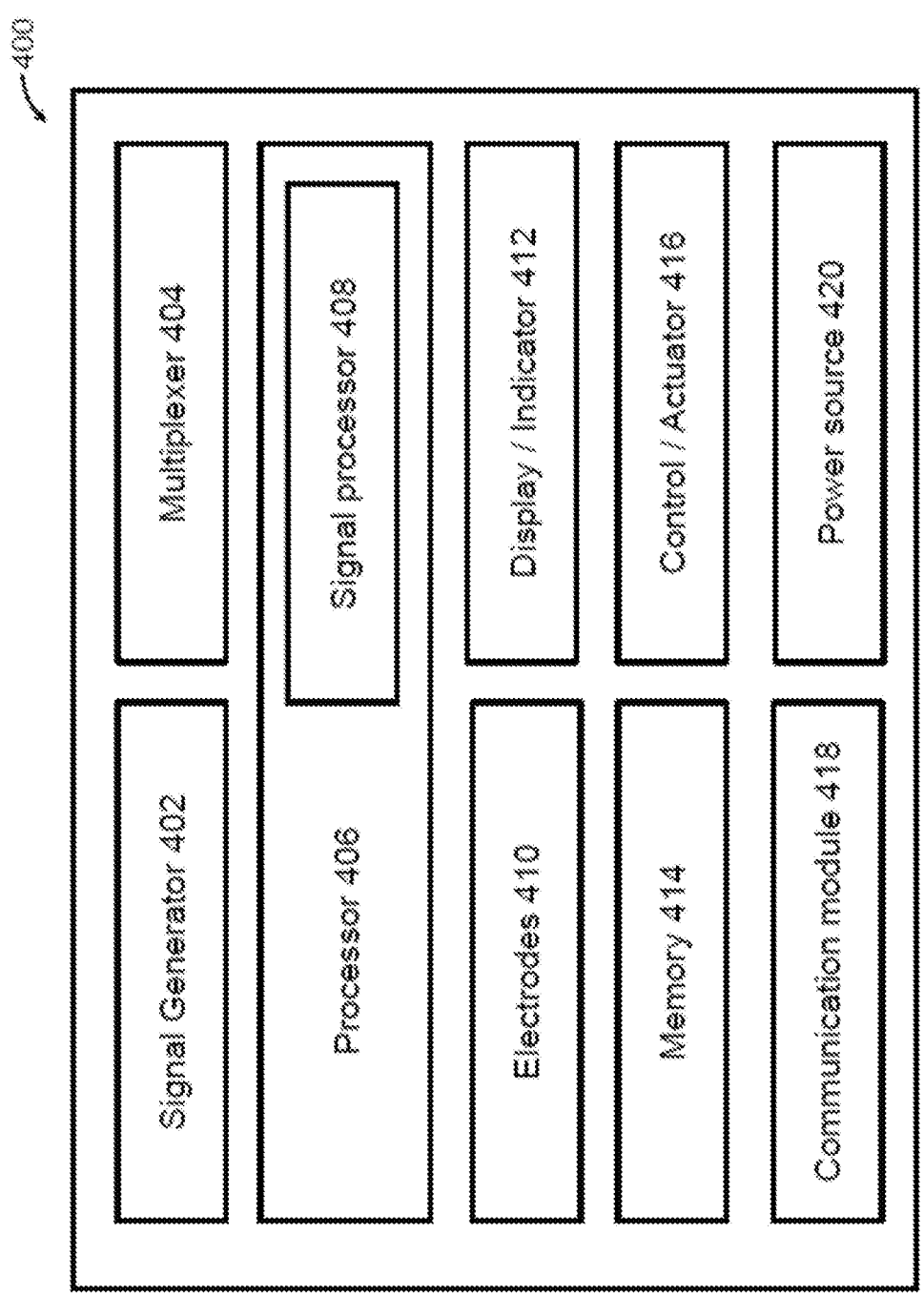
FIG. 4 is a functional block diagram of a wearable gesture recognition device in accordance with one embodiment of the invention.

FIG. 4 shows functional block diagram of a wearable gesture recognition device 400 in accordance with one embodiment of the invention. The wristband 200 and watch 300 in FIGS. 2-3B may include like or the same configuration as that illustrated in FIG. 4.

The device 400 includes electrodes 410 arranged to be arranged on a body part of a wearer. The electrodes 410 may be the same as the electrodes 204, 304 shown in FIGS. 2-3B. The electrodes 410 may each be adapted to operate as both transmission electrode and receiving electrode. A multiplexer 404 is arranged to select at least one of the electrodes 410 as transmission electrode and to select at least one of the remaining electrodes as receiving electrode. The multiplexer may be controlled by the processor 406, to implement a predetermined electrode excitation scheme, to select different electrodes 410 as transmission electrode at different instances.

A signal generator 402, e.g., in the form of a waveform generator, is arranged to provide a waveform signal to the electrode(s) selected to be transmission electrode for transmission of a respective excitation signal to the body part of the wearer. In operation, the signal generator 402 may provide different waveform signals to different transmission electrode, and it may transmit waveform signals to multiple transmission electrodes at the same time. Upon transmission of the excitation signals, one or more of the remaining electrodes 410 may be selected as receiving electrodes to receive response signal as a result of the respective excitation signal.

A signal processor 408, as part of a processor 406, is arranged to process the respective response signal received by at least one of the remaining electrodes as a result of the respective excitation signal, for determination of an electrical impedance tomogram for gesture recognition. The signal processor may perform various signal processing, comprising ADC, DAC, noise suppression, SNR boost, filtering, etc. The data processed by the signal processor may either be transmitted to an external electronic device or server through the communication module for further processing, or may be further processed by the processor 406. The further processing comprises determination of the electrical impedance tomogram for gesture recognition, preferably using one or more of the method steps 108-116 in FIG. 1.

In the present embodiment, the processor may be implemented using one or more MCU, controller, CPU, logic gates components, ICs, etc. In one embodiment, the processor is further arranged to process signals and data associated with the determined gesture, the determined response associated with the determined gesture, etc.

The device 400 also includes a memory module 414. The memory module 414 may include a volatile memory unit (such as RAM), a non-volatile unit (such as ROM, EPROM, EEPROM and flash memory) or both. The memory module 414 may be used to store program codes and instructions for operating the device. Preferably, the memory module 414 may also store data processed by the signal processor 408 or the processor 406.

A display or indicator 412 may be provided in the device 400. The display 412 may be an OLED display, a LED display, a LCD display. The display 412 may be touch-sensitive to receive user input. In some embodiments, the device 400 may include indicators in the form of, e.g., LEDs.

The device 400 may also include one or more actuators 416 arranged to receive input from the user. The actuators 416 may be any form and number of buttons, toggle switch, slide switch, press-switch, dials, etc. The user may turn on or off the device 400 using the actuators 416. The user may input data to the device 400 using the actuators 416.

A power source 420 may be arranged in the device 400 for powering the various modules. The power source may include Lithium-based battery. The power source 420 is preferably a rechargeable power source. In one example, the rechargeable power source may be recharged through wired means such as charging port provided on the device. Alternatively, the rechargeable power source may be recharged wirelessly through induction.

The device 400 includes a communication module 418 arranged to communicate information and data between the wearable gesture recognition device 400 and one or both of: an external electronic device and a server. The external electronic device may be a mobile phone, a computer, or a tablet. The server may be a cloud computing server that is preferably implemented by combination of software and hardware. The communication module may be a wired communicate module, a wireless communication module, or both. In the embodiment with a wireless communication module, the module 418 preferably includes a Bluetooth module, in particular a Low energy Bluetooth module. However, in other embodiments, the wireless communication module may alternatively or also include LTE-, Wi-Fi-, NFC-, ZigBee-communication modules.

In one embodiment of the invention, the communication module 418 is arranged to transmit, to the external electronic device or the server, signals processed by the signal processor, for determination of the electrical impedance tomogram for gesture recognition. The communication module 418 may also be arranged to receive, from the external electronic device or the server: signals indicative of a gesture determined based on the determined electrical impedance tomogram, or signals indicative of a response determined based on the determined electrical impedance tomogram.

A person skilled in the art would appreciate that the modules illustrated in FIG. 4 can be implemented using different hardware, software, or a combination of both. Also, the device may include additional modules or include fewer modules (some omitted). Although not clearly illustrated, the various modules in the device 400 are operably connected with each other, directly or indirectly.

Figure 5:
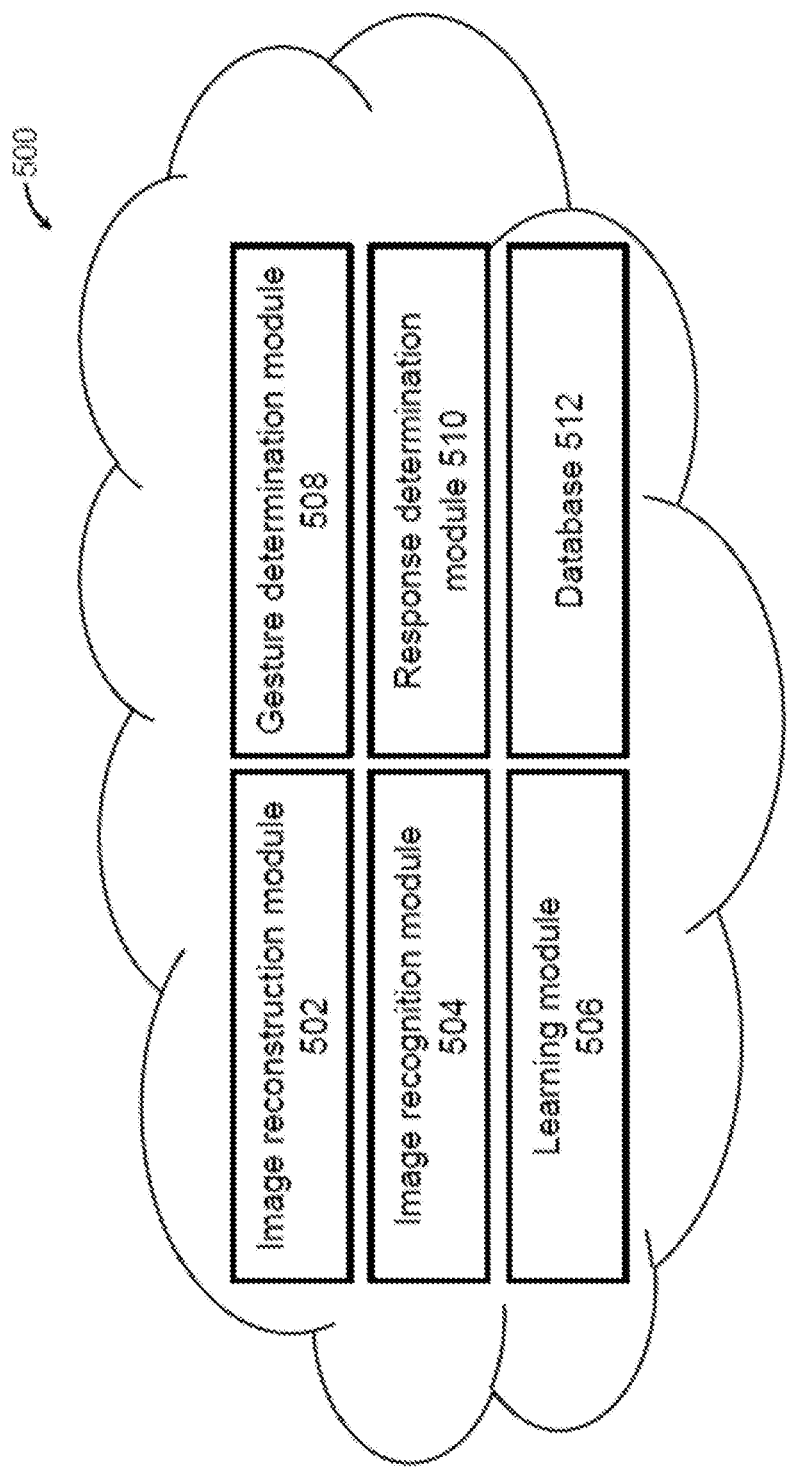
FIG. 5 is a functional block diagram of a server, in the form of a cloud computing server, in accordance with one embodiment of the invention.

FIG. 5 shows a server 500, in the form of a cloud computing server, in accordance with one embodiment of the invention, arranged to operate with the devices 200, 300, and 400 of FIGS. 2-4.

The server 500 is arranged to communicate data with the device 200, 300, 400, directly, or indirectly through an external electronic device. In one embodiment, the server 500 is arranged to receive, from the device 200, 300, 400, signals processed by the signal processor 408, for determination of the electrical impedance tomogram for gesture recognition. In another embodiment, the server 500 is arranged to receive, from the external electronic device operably connected with the device 200, 300, 400, signals processed by the signal processor 408, for determination of the electrical impedance tomogram for gesture recognition The server 500 includes an image reconstruction module 502 arranged to reconstruct an electrical impedance tomogram based on signals received from the communication module of the device 200, 300, 400. The reconstruction may include performing back-projection, SNR boost, artifact correction, image correction, registration, co-registration, normalization, etc.

The server 500 also includes an image recognition module 504 arranged to compare the reconstructed electrical impedance tomogram with predetermined electrical impedance tomograms in a database 512 to determine a matching. The predetermined electrical impedance tomograms in the database each correspond to a respective gesture. The image recognition module 504 determines the predetermined electrical impedance tomogram that is most similar to the reconstructed electrical impedance tomogram. In one example, the image recognition module 504 may determine that there is no matching, in which case a response may be provided back to the device 200, 300, 400, or the external electronic device operably connected with the device 200, 300, 400.

The gesture determination module 508 determines, based on the determined matching result provided by the image recognition module, a predetermined gesture associated with the reconstructed electrical impedance tomogram. The predetermined gesture and its associated with the predetermined electrical impedance tomogram may be set by the user, using an application on an external electronic device, and stored in the server.

The server also includes a response determination module 510 arranged to determine a response based on the determined gesture. The response associated with respective gesture is predetermined, e.g., set by the user, using an application on an external electronic device, and stored in the server. The response determination module 510 may transmit signals indicative of the determined response to a device or system to be controlled to affect operation thereof. Alternatively, the response determination module 510 may transmit signals indicative of the determined response to the device 200, 300, 400, which in turn provides control signal to the device or system to be controlled to affect operation thereof.

Preferably, the server 500 includes a training module 506 that learns, using machine learning method, based on signals received from the communication module, the reconstructed electrical impedance tomogram, the matching result, etc. The training module 506 trains the database 512 accordingly to improve matching accuracy and speed.

A person skilled in the art would appreciate that one or more of the modules in the server 500 may be implemented on the device 200, 300, 400, on an external electronic device connected to the device 200, 300, 400, or on both.

Figure 6:
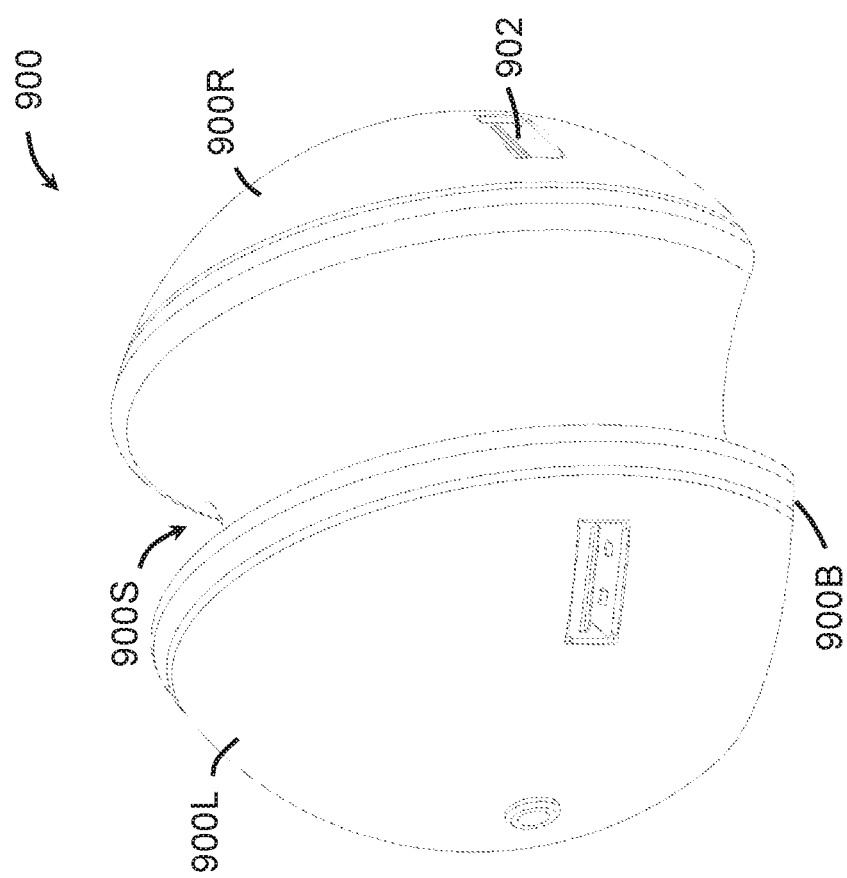
FIG. 6 is an illustration of a charger for the wearable gesture recognition device of FIG. 2 in accordance with one embodiment of the invention.

FIG. 6 shows a charger 900 for the device 200 in one embodiment of the invention. The charger 900 has a body with flat base 900B and two generally hemi-spherically shaped sides 900L, 900R. An annular slot 900S is arranged between the two hemi-spherically shaped sides 900L, 900R for receiving the device 200. Means for securing the device 200 to the charger slot 900S may include a mechanical lock, a magnetic lock, etc. In one example, the device 200 includes a magnetic lock member and the charger includes, in the slot 900S, corresponding magnetic lock member that can lock and align the device 200 in the slot 900S. On two sides of the body are USB ports, for receiving data/power from an external electronic device, or for transmitting data/power to an external electronic device, through a cable. In other embodiments the USB ports may be replaced with data/power ports of other standards, e.g., lightning port. The charger 900 may incorporate or be an information handling system described in further detail below.

FIG. 7 shows a ring 1000 arranged to operate with the device 200, 300 to improve the measurement accuracy or functions of the device 200, 300. The ring 1000 may be suitably sized to eh worn on a finger of the user. In one embodiment, the ring 1000 may be of like construction of the device 200, 300. The ring 1000 may be arranged to communicate with the device 200, 300 using Bluetooth, near field communication, or other wireless communication protocol. The ring may include electrodes, which function as a reference point, or as those on the device 200, 300, to provide improved gesture recognition accuracy. In some embodiments, the ring 1000 may incorporate or be an information handling system described in further detail below.

FIGS. 8A to 8D illustrated various systems incorporating a wearable gesture recognition device 200, 300 in accordance with one embodiment of the invention. Systems 800A-800B include the wearable gesture recognition device 200, 300, an external electronic device 700 in the form of a mobile phone, a server 500A-500D with similar or the same construction of server 500, and a system or device to be controlled based on the recognized gesture 10. Systems 800C-800D include all these components except the external electronic device 700. In these embodiments, the system or device to be controlled based on the recognized gesture 10 may be any computing system, e.g., smart phone control module, smart home control module, computer, etc.

Figure 8A:
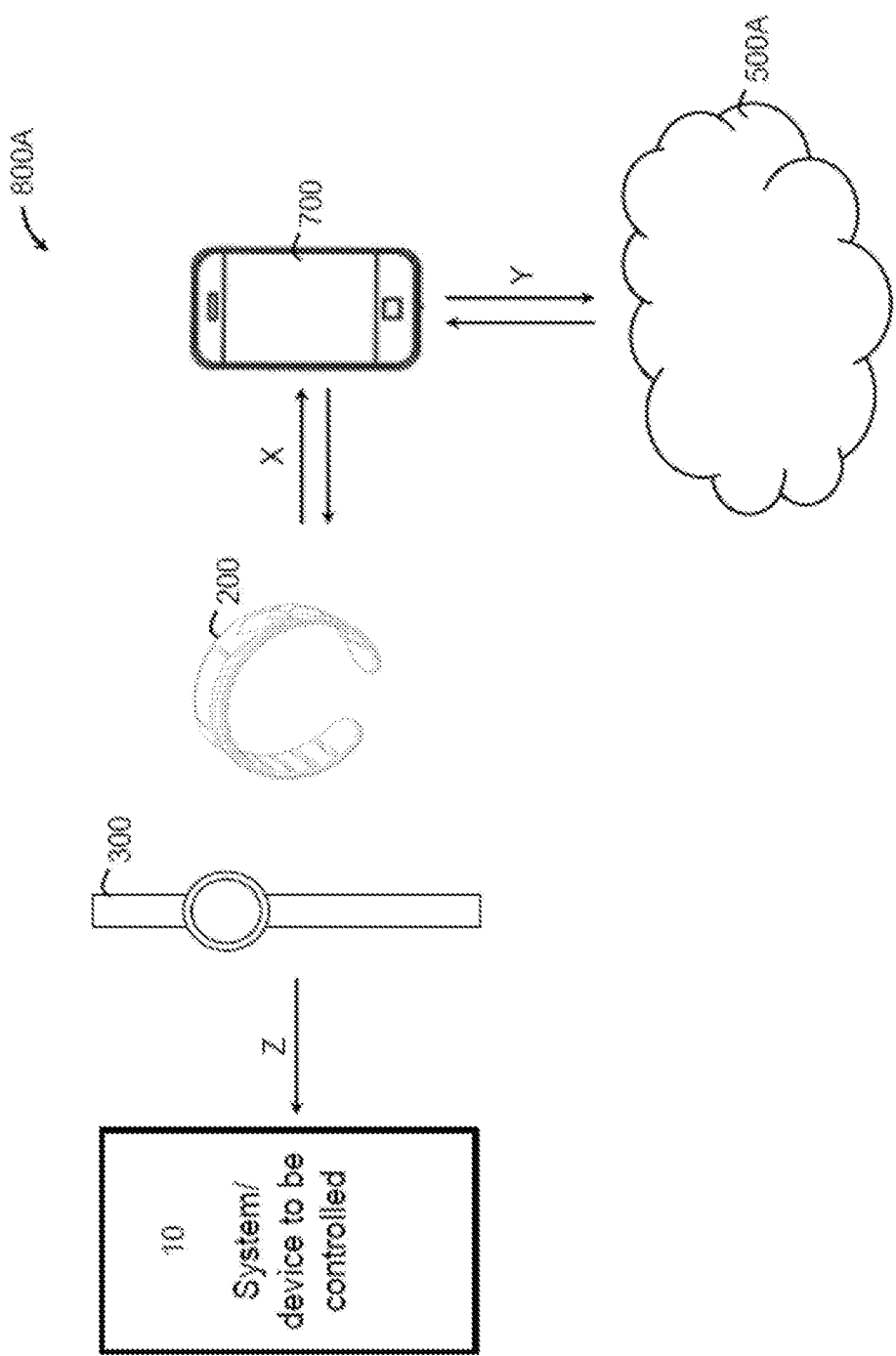
FIG. 8A is a system incorporating a wearable gesture recognition device in accordance with one embodiment of the invention.

The embodiment of the system 800A in FIG. 8A, the device 200, 300 in system 800A detects response signal received in response to the excitation signals provided by the electrodes. The device 200, 300 transmits the processed signal to the smart phone 700 and hence to the server 500A. The communication link X between the device 200, 300 and the phone 700 may be a wireless communication link such as a Bluetooth communication link. The communication link Y between the phone 700 and the server 500A may be a wireless communication link such as a cellular communication link. The server 500A in this example may be arranged to process the processed signal transmitted from the device 200, 300, for: reconstruction of an electrical impedance tomogram, determination of gesture associated with the reconstructed electrical impedance tomogram, determination of response based on the determined gesture, etc. The server 500A may perform one or more of these steps and transmit the result to the device 200, 300 or the phone 700, via links X and Y, for performing the remaining steps. In this embodiment, the server 500A transmits signals indicative of the determined response to the device 200, 300, which in turn provide a control signal via communication link Z to the device or system to be controlled 10 to affect operation of the device or system. The communication link is preferably a wireless communication link.

The embodiment of the system 800B in FIG. 8B is the same as that in FIG. 8A, except that the signals indicative of the determined response is transmitted directly by the server 500B to the device to be controlled, via a communication link W. In this embodiment, it is preferably that no direct connection is required between the device 200, 300 and the device to be controller 10.

Figure 8C:
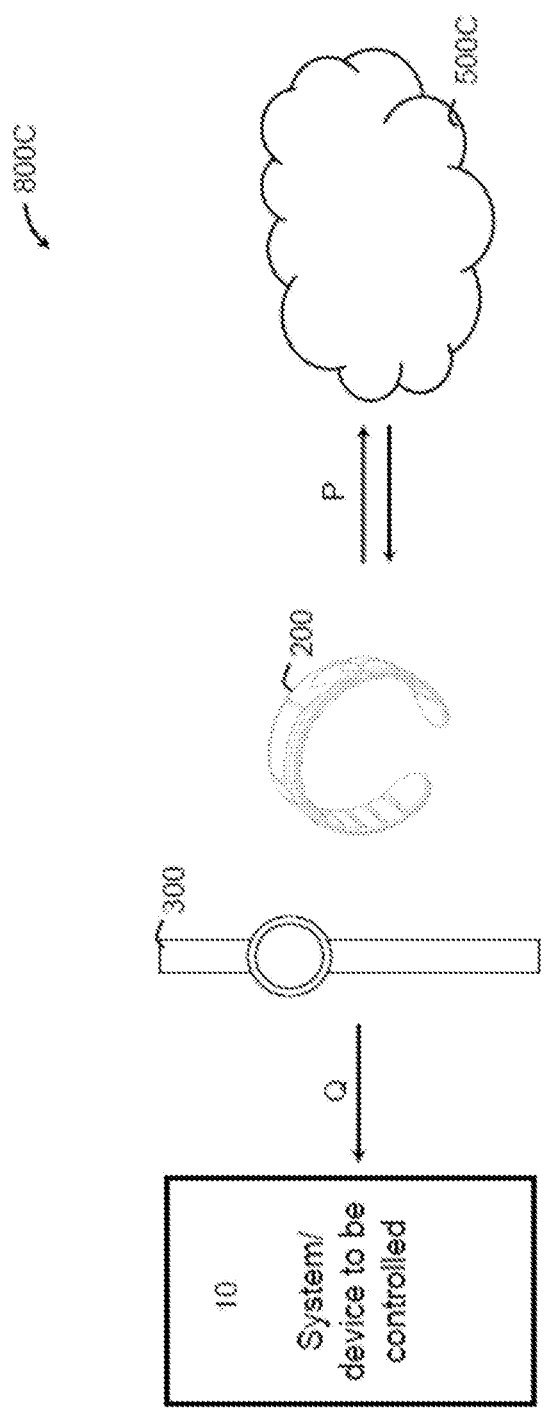
FIG. 8C is a system incorporating a wearable gesture recognition device in accordance with one embodiment of the invention.

The embodiment of the system 800C in FIG. 8C is the same as that in FIG. 8A, except that the smart phone 700 is omitted. In this embodiment, the device 200, 300 is in direct communication with the server 500C through communication link P. Communication link P is preferably a wireless communication link such as a cellular or Wi-Fi communication link. The server 500C, upon determining the result, transmits the result to the device 200, 300, to allow the device 200, 300 to provide control signal via communication link Q to the system or device to be controlled 10. Communication link Q is preferably a wireless communication link.

Figure 8D:
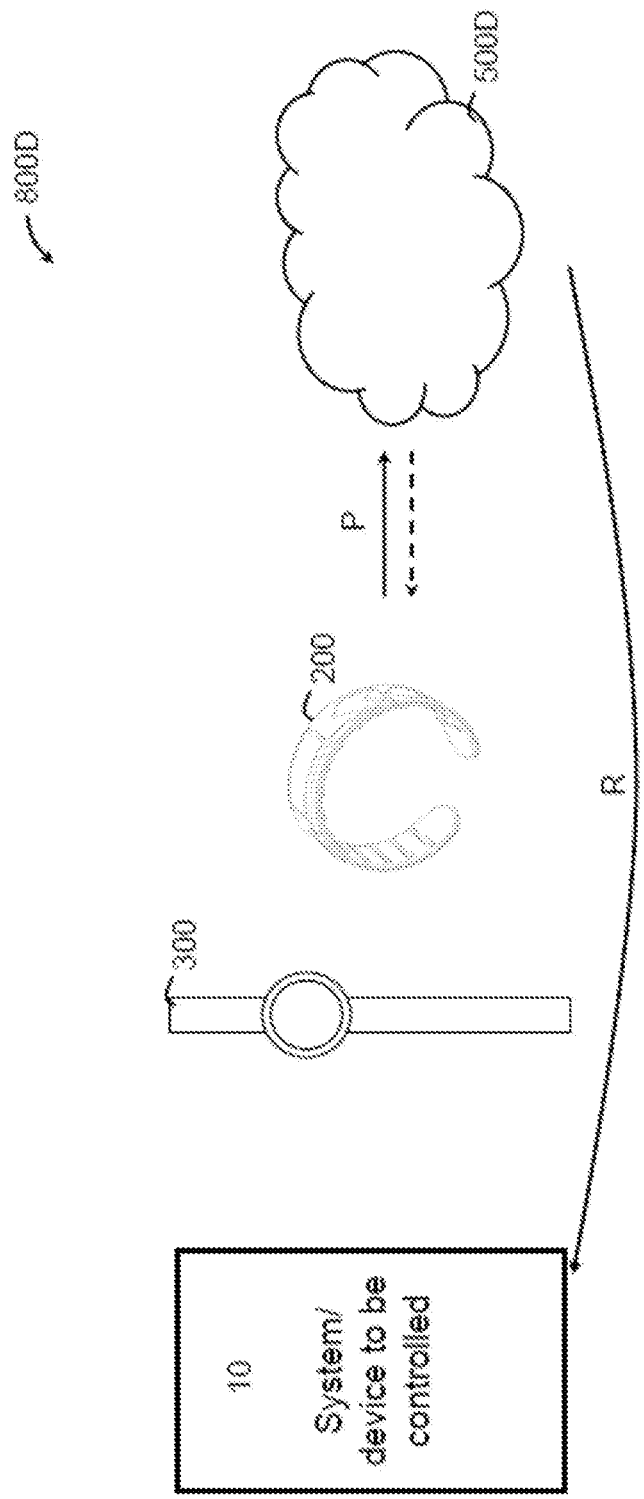
FIG. 8D is a system incorporating a wearable gesture recognition device in accordance with one embodiment of the invention.

The embodiment of the system 800D in FIG. 8D is the same as that in FIG. 8C, except that the signals indicative of the determined response is transmitted directly by the server 500D to the device to be controlled, via a communication link R, preferably wireless. In this embodiment, it is preferably that no direct connection is required between the device 200, 300 and the device to be controller 10.

The server 500, 500A-500D, charger 900, ring accessory 1000, and external electronic device 700 in FIGS. 5-8D may be implemented using one or more of the following exemplary information handling system. The information handling system may have different configurations, and it generally comprises suitable components necessary to receive, store and execute appropriate computer instructions or codes. The main components of the information handling system are a processing unit and a memory unit. The processing unit is a processor such as a CPU, an MCU, etc. The memory unit may include a volatile memory unit (such as RAM), a non-volatile unit (such as ROM, EPROM, EEPROM and flash memory) or both. Optionally, the information handling system further includes one or more input devices such as a keyboard, a mouse, a stylus, a microphone, a tactile input device (e.g., touch sensitive screen) and a video input device (e.g., camera). The information handling system may further include one or more output devices such as one or more displays, speakers, disk drives, and printers. The displays may be a liquid crystal display, a light emitting display or any other suitable display that may or may not be touch sensitive. The information handling system may further include one or more disk drives which may encompass solid state drives, hard disk drives, optical drives and/or magnetic tape drives. A suitable operating system may be installed in the information handling system, e.g., on the disk drive or in the memory unit of the information handling system. The memory unit and the disk drive may be operated by the processing unit. The information handling system, also preferably includes a communication module for establishing one or more communication links (not shown) with one or more other computing devices such as a server, personal computers, terminals, wireless or handheld computing devices. The communication module may be a modem, a Network Interface Card (NIC), an integrated network interface, a radio frequency transceiver, an optical port, an infrared port, a USB connection, or other interfaces. The communication links maybe wired or wireless for communicating commands, instructions, information and/or data. Preferably, the processing unit, the memory unit, and optionally the input devices, the output devices, the communication module and the disk drives are connected with each other through a bus, a Peripheral Component Interconnect (PCI) such as PCI Express, a Universal Serial Bus (USB), and/or an optical bus structure. In one embodiment, some of these components maybe connected through a network such as the Internet or a cloud computing network. The external electronic device may be a mobile phone, a computer, or a tablet. The server may be a cloud computing server that is preferably implemented by combination of software and hardware.

The wearable gesture recognition device and system in the above embodiments of the invention can be connected with different systems and devices, directly or through the server, for controlling these systems and devices. Exemplary applications including:

(1) Smartphone Control

The recognized gesture may be used to control operation of the smart phone. For example, fisting the hand would lock the screen of the phone, trigger the phone to capture an image, etc.

(2) Smart Home Control

The recognized gesture may be used to control operation of the smart phone. For example, fisting the hand would switch off the lights, straightening two fingers may switch on two lights, three fingers three lights, etc.

(3) Music Gesture Training

The recognized gesture may be used as part of a musician training program to determine posture or even force applied during various instances to assist, for example, Violin Training.

(4) Sports Gesture Training

The recognized gesture may be used as part of a sports training program to determine posture or even force applied during various instances to assist, for example, javelin throw training.

(5) VR/AR Gaming

The recognized gesture may be used as part of a gaming system as game control (user input).

(6) Sign Language Translation

The recognized gesture may be used for real-time sign language translation. For example, real time conversion of sign language to text on computer screen, to assist translation of sign language.

(7) Rapid Preliminary Medical Screening

The recognized gesture may be used for real-time preliminary medical screening of disease associated with body parts on which the device is worn. In one specific example, the device can be used for carpal tunnel syndrome (CTS) screening. CTS is a common medical condition that causes pain, numbness, and tingling in the hand and arm, generally caused by compression of the median nerve at the wrist. Existing clinical diagnosis of CTS uses nerve conduction studies and ultrasound in hospitals, which are relatively complicated and require long wait-time (due to the large demand and the relatively little resource in the hospitals). In one example, the wristband provides a portable imaging modality with the capability to capture cross sectional plane of the wrist at high speed (<1 min). As such the cross sectional area of the median nerve within or near the carpal tunnel can be readily measured for assessment.

Although not required, the embodiments described with reference to the Figures can be implemented as an application programming interface (API) or as a series of libraries for use by a developer or can be included within another software application, such as a terminal or personal computer operating system or a portable computing device operating system. Generally, as program modules include routines, programs, objects, components and data files assisting in the performance of particular functions, the skilled person will understand that the functionality of the software application may be distributed across a number of routines, objects or components to achieve the same functionality desired herein.

It will also be appreciated that where the methods and systems of the invention are either wholly implemented by computing system or partly implemented by computing systems then any appropriate computing system architecture may be utilized. This will include stand-alone computers, network computers and dedicated hardware devices. Where the terms "computing system" and "computing device" are used, these terms are intended to cover any appropriate arrangement of computer hardware capable of implementing the function described.

It will be appreciated by persons skilled in the art that numerous variations and/or modifications may be made to the invention as shown in the specific embodiments without departing from the spirit or scope of the invention as broadly described. For example, the wearable gesture recognition device may take various form not limited to the one illustrated in FIGS. 2-3B. The wearable gesture recognition device need not be wrist worn but may be worn on any other parts of the body of the user. The signal processing may be performed substantially entirely on the wearable gesture recognition device, partly on the wearable gesture recognition device and partly on the server or external electronic device, or substantially entirely on the server or external electronic device. The device or system to be controlled based on the gesture determined can be any electronic device operable to communicate with the wearable gesture recognition device or the server, directly or indirectly. The wearable gesture recognition device may further include an IMU arranged to determine movement of the wearable gesture recognition device to affect determination of the electrical impedance tomogram. The wearable gesture recognition device may further include one or more biosensors arranged to detect physiological signals of the wearer to affect determination of the electrical impedance tomogram. The one or more biosensors may be any of: a blood oxygen level sensor; a pulse rate sensor; a heart rate sensor; and an EMG detector. The wearable gesture recognition device may further include a GPS module arranged to determine location of the wearable gesture recognition device. The determined location may optionally be used to affect determination of the electrical impedance tomogram. The present embodiments are, therefore, to be considered in all respects as illustrative and not restrictive.

The invention claimed is:

1. A method of medical screening using a wearable medical screening device arranged to be worn on a wrist of a wearer, the method comprising:
    arranging the wearable medical screening device with a plurality of electrodes on the wrist of the wearer;
    providing a signal to at least one of the plurality of electrodes for transmission of a respective excitation signal to the wrist of the wearer; and
    processing a respective response signal received by at least one of remaining electrodes of the plurality of electrodes as a result of the respective excitation signal, to thereby determine an electrical impedance tomogram for real-time preliminary medical screening of carpal tunnel syndrome associated with the wrist on which the wearable medical screening device is worn.

2. The method of claim 1, further comprising communicating information and data between the wearable medical screening device and one or both of:
    an external electronic device and a server.

3. The method of claim 2, further comprising reconstructing an electrical impedance tomogram based on the signals processed by the wearable medical screening device.

4. The method of claim 1, further comprising:
    selecting at least one of the plurality of electrodes as transmission electrode and at least one of the remaining electrodes as receiving electrode.

5. The method of claim 1, further comprising determining at least one of movement of the wearable medical screening device and physiological signals of the wearer to affect determination of the electrical impedance tomogram.

6. A wearable medical screening device arranged to be worn on a wrist of a wearer, comprising:
    a plurality of electrodes arranged to be arranged on the wrist of the wearer;
    a signal generator arranged to provide a signal to at least one of the plurality of electrodes for transmission of a respective excitation signal to the wrist of the wearer; and
    a signal processor arranged to process a respective response signal received by at least one of remaining electrodes of the plurality of electrodes as a result of the respective excitation signal, to thereby determine an electrical impedance tomogram for real-time preliminary medical screening of carpal tunnel syndrome associated with the wrist on which the wearable medical screening device is worn.

7. The wearable medical screening device of claim 6, further comprising a communication module arranged to communicate information and data between the wearable medical screening device and one or both of: an external electronic device and a server; wherein the communication module is arranged to transmit, to the external electronic device or the server, signals processed by the signal processor, for determination of the electrical impedance tomogram.

8. The wearable medical screening device of claim 7, wherein the external electronic device or the server is arranged to:
    reconstruct an electrical impedance tomogram based on signals received from the communication module.

9. The wearable medical screening device of claim 6, wherein the plurality of electrodes are arranged to operate as both transmission electrode and receiving electrode.

10. The wearable medical screening device of claim 6, further comprising a multiplexer arranged to select at least one of the plurality of electrodes as transmission electrode and to select at least one of the remaining electrodes as receiving electrode.

11. The wearable medical screening device of claim 6, wherein the plurality of electrodes are contact-type electrodes.

12. The wearable medical screening device of claim 6, wherein the plurality of electrodes are non-contact-type electrodes.

13. The wearable medical screening device of claim 6, further comprising an IMU arranged to determine movement of the wearable medical screening device to affect determination of the electrical impedance tomogram.

14. The wearable medical screening device of claim 6, further comprising one or more biosensors arranged to detect physiological signals of the wearer to affect determination of the electrical impedance tomogram.

15. The wearable medical screening device of claim 14, wherein the one or more biosensors comprise a blood oxygen level sensor.

16. The wearable medical screening device of claim 14, wherein the one or more biosensors comprise a pulse rate sensor.

17. The wearable medical screening device of claim 14, wherein the one or more biosensors comprise a pressure sensor.

18. The wearable medical screening device of claim 14, wherein the one or more biosensors comprise a temperature sensor.

19. The wearable medical screening device of claim 14, wherein the one or more biosensors comprise a heart rate sensor.

20. The wearable medical screening device of claim 14, wherein the one or more biosensors comprise an EMG detector.

21. The wearable medical screening device of claim 6, wherein the plurality of electrodes are spaced apart substantially equally.

22. The wearable medical screening device of claim 6, further comprising a flexible body arranged to be worn by the wearer and on which the plurality of electrodes are arranged, and the flexible body is arranged to be fit onto the wearer by inherent resilience.

* * * * *